United States Patent
Kuhn

(10) Patent No.: US 7,397,887 B2
(45) Date of Patent: Jul. 8, 2008

(54) COMPUTERIZED TOMOGRAPHIC IMAGING SYSTEM

(75) Inventor: Michael Harald Kuhn, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/549,136

(22) PCT Filed: Mar. 4, 2004

(86) PCT No.: PCT/IB2004/000691

§ 371 (c)(1),
(2), (4) Date: Sep. 13, 2005

(87) PCT Pub. No.: WO2004/080310

PCT Pub. Date: Sep. 23, 2004

(65) Prior Publication Data

US 2006/0193430 A1    Aug. 31, 2006

(30) Foreign Application Priority Data

Mar. 13, 2003 (EP) .................................. 03100642

(51) Int. Cl.
*G01N 23/00* (2006.01)

(52) U.S. Cl. .................. 378/9; 378/19; 378/901

(58) Field of Classification Search .............. 378/4, 378/9, 15, 19, 62, 901; 600/425, 428

See application file for complete search history.

(56) References Cited

U.S. PATENT DOCUMENTS

| 5,533,080 | A | 7/1996 | Pelc |
| 5,966,422 | A | 10/1999 | Dafni |
| 6,198,790 | B1 | 3/2001 | Pflaum |
| 6,421,412 | B1 | 7/2002 | Hsieh et al. |
| 7,085,343 | B2 * | 8/2006 | Shinno et al. .................. 378/9 |
| 2005/0089134 | A1 * | 4/2005 | Bruder et al. .................. 378/9 |

FOREIGN PATENT DOCUMENTS

| DE | 10302565 A1 * | 8/2004 |
| WO | WO 02/26134 A1 | 4/2002 |

OTHER PUBLICATIONS

Crawford, C.R., et al.; Computed tomography scanning with simultaneous patient translation; 1990; Med. Phys.; 17(6):967-982.

* cited by examiner

*Primary Examiner*—Irakli Kiknadze

(57) ABSTRACT

In cardiac CT, it is the goal to acquire data for a full scan as fast as possible. For this reason, gantry rotation is increased further and further, such that the G-forces on the tube of the devices on the gantry become a limiting factor. Alternatively, the temporal resolution of scans can be doubled by mounting two complete tube-detector assemblies onto the gantry. However, this solution doubles the costs for the tube-detector assembly. According to the present invention it is proposed to modify one of the tube-detector assemblies such that one detector has a reduce size. Then, information from another detector is used to supplement scanning results from the detector with reduced size.

12 Claims, 5 Drawing Sheets

COMPUTERIZED TOMOGRAPHIC IMAGING SYSTEM

This invention relates generally to computer tomographic (CT) imaging and more particularly, to generating images of a heart. In particular, the present invention relates to a computerized tomographic imaging system for generating an image of an object of interest, a method of generating an image of an object of interest and to a computer product which may be executed on a computerized tomographic imaging system.

In a known CT system, an x-ray source projects a fan-shaped beam, which is collimated to lie within an X-Y plane of a Cartesian coordinate system. This plane is usually referred to as an "imaging plane". The x-ray beam passes through the object of interest such as for example a patient. After being attenuated by the object of interest, the radiation of the beam impinges upon a radiation detector. The intensity of the attenuated beam radiation detected by the detector is dependent upon the attenuation of the x-ray beam by the object of interest. The detector comprises a plurality of detector elements. Each detector element produces a separate electrical signal that is a measurement of the intensity of the attenuated beam at the detector location. The attenuation measurements from all the detectors are acquired separately to produce a transmission profile. The x-ray source and the detector are mounted to a gantry which rotates around the object of interest so that an angle at which the x-ray beam intersects the object of interest changes constantly. A group of x-ray attenuation measurements (projection data) from the detector at one gantry angle is referred to as a "view". It may also be referred to as a "profile". A "scan" of the object comprises a set of views made at different gantry angles during one revolution (at least 180 degrees plus fan angle) of the x-ray source and detector. The scan data consisting of the plurality of views is further processed to reconstruct an image that corresponds to a two dimensional slice taken through the object. Recently, scanners have become common which have a number of parallel detector arrays, such that the fan beam is widened in the direction perpendicular to the respective x-y-plane, thus allowing to acquire 2-dimensional views (profiles) at the same time.

A common method for reconstructing an image from the scan data is the filtered back projection. After this reconstruction step, including proper calibration, the image data of the scan is related to integers which are referred to as "Hounsfield units" which may be displayed as brightness points at a display.

In order to reduce a scan time, i.e. a time necessary to acquire the scan data, the patient is displaced along a horizontal axis intersecting a center of the gantry while the gantry is rotated around the object of interest. Instead of moving the object of interest through the gantry, it is also possible to keep the object stationary while displacing the gantry. These movements create a helical scanning path along which the radiation source and the detector are rotated and displaced around the object of interest during a scan. Such a system generates a single helix from a single fan beam helical scan. The helix mapped out by the fan beam yields projection data from which images in each prescribed slice may be reconstructed. Helical reconstruction algorithms are known and described for example in C. Crawford and K. King, "Computed Tomography Scanning with Simultaneous Patient Translation," Med. Phys. 17(6), November/December 1990.

In order to generate images of rapidly moving objects such as a heart, known systems have been operated at an increased gantry speed. In other words, in cardiac CT, in order to acquire the data for a full scan as fast as possible to observe/resolve the motion of for example coronary arteries over time, the gantry rotation on current scanners is increased further and further. However, now the gantry speed is increased to such an extent that the G-forces on the radiation tube and other devices on the gantry become a limiting factor.

Alternatively, the temporal resolution of the scans may be doubled by mounting two complete tube-detector assemblies onto the gantry. However, as obvious to the skilled person, such a solution doubles the cost of the tube-detector assembly and is associated with a shortage of mechanical space on the circumference of the gantry.

Reference U.S. Pat. No. 6,421,412 B1 discloses a dual cardiac CT scanner, where two source-detector pairs are utilized to generate images of the entire heart without significant motion artifacts. By collecting projection data for a limited field of view containing only the heart, the size of the detector array is reduced and minimized motion artifact images are generated by collecting $\pi$ plus a fan angle, which is the angle of the beam projected from the x-ray source, of protection data.

In the known CT systems, the detector arrays of the two source detector pairs have the same size. Accordingly, the dimensions of the fan beam or cone beam emitted by each of the radiation sources are the same and the power emitted from the sources is the same too. Accordingly, a patient scanned by such an assembly is exposed to the same radiation power by each of the radiation sources.

It is an object of the present invention to minimize the radiation to which the object of interest is subjected, while at the same time minimizing the cost and space occupied by the source-detector assemblies According to an exemplary embodiment of the present invention, the above object is solved with a computerized tomographic imaging system for generating an image of an object of interest comprising a first source-detector pair. The first source-detector pair comprises a first radiation source and a first radiation detector having a first number of detector elements. The first radiation source emits a first radiation beam towards the first radiation detector such that the first radiation beam traverses the object of interest and impinges onto the first radiation detector. Furthermore, there is provided a second source-detector pair. The second source-detector source-detector pair comprises a second radiation source and a second radiation detector with a second number of detector elements, wherein the second radiation source emits a second radiation beam towards the second radiation detector such that the second radiation beam traverses the object of interest and impinges onto the second radiation detector. The second number is smaller than the first number.

Advantageously, according to the present invention, the second radiation detector has a smaller number of detector elements than the first radiation detector. By this, the costs of the source-detector assembly can be reduced significantly, and it consumes less space in circumferential direction on the gantry. In addition to that, the radiation to which the object of interest is subjected can be reduced since the radiation power emitted by the second radiation source can be adapted to the smaller size of the second detector and can thereby be reduced. Hence, according to the present invention, the costs for the source-detector assembly are reduced and the patient dose or radiation dose subjected to the object of interest can be reduced significantly.

According to an exemplary embodiment, the second readout from the second radiation detector is supplemented with data obtained from measurements from the first readout from the first radiation detector. These data are generated from the reconstructed image obtained from the projection data obtained from the first source-detector assembly. Since for this assembly, an image can readily be reconstructed, it is possible to compute the measurements missing for the second source-detector arrangement by calculating the line integral over the attenuation in the object along the projection direction corresponding to the 'missing' detector elements. This computation is likely to correspond to the true data because the part of the body through which the respective rays are passing are not rapidly moving, while the attenuation along the rays through the moving heart are directly measured by the second detector. By this, first and second readouts can be generated having the same size simulating two detectors having the same size. Readouts may be provided to a conventional CT system for reconstructing the image in accordance, for example, with C. Crawford and K. King, "Computed Tomography Scanning with Simultaneous Patient Translation", Med. Phys. 17 (6), November/December 1990.

According to another exemplary embodiment, the readouts from the detector cells of the first radiation detector which are used for supplementing the second readouts are selected such that these detector cells are in an area of the first radiation detector by which the first detector exceeds the second radiation detector. By this, advantageously, two complete data sets, namely two complete first and second readouts can be provided, which may be used for further processing. By this, while minimizing motion artifacts in the final image, a high image quality can be ensured and the system according to the present invention can easily be adapted and implemented to in a known CT-scanner image reconstruction system.

According to another exemplary embodiment, the computerized tomographic imaging system is a dual tube cardiac CT system.

According to another exemplary embodiment, a method of generating an image of an object of interest is provided where the object of interest is scanned by means of a first source-detector pair. The first source-detector pair comprises a first radiation source and a first radiation detector. The first radiation source emits a first radiation beam towards the first radiation detector such that the first radiation beam traverses the object of interest and impinges onto the first radiation detector. Furthermore, the object of interest is scanned by means of a second source-detector pair, wherein the second source-detector pair comprises a second radiation source and a second radiation detector. The second radiation source emits a second radiation beam towards the second radiation detector such that the second radiation beam traverses the object of interest and impinges onto the second radiation detector. First readouts are read from the first radiation detector and second readouts are read from the second radiation detector. The image is generated from the first and second readouts, wherein for generating the image, a first number of elements from the first readout and a second number of elements from the second readout are used. The first number of elements corresponds to first detector elements of the first radiation detector and the second number of elements corresponds to second detector elements of the second radiation detector. The second number is smaller than the first number.

Advantageously, the method according to this exemplary embodiment of the present invention may be implemented in a known CT system having two detectors with the same size. However, according to the present invention only a reduced number of detector cells are read from one of the detectors. By this, a radiation power emitted by the corresponding source can be reduced and thereby a radiation dose to which the object of interest or patient is subjected can be reduced.

It may be seen as the gist of an exemplary embodiment of the present invention that the size/number of detector elements of one detector of a plurality of detectors used for example for a cardiac CT is reduced. Thereby, advantageously, a radiation dose to which the object of interest or the patient is subjected can be reduced and the costs of the source-detector assembly can be reduced too.

These and other aspects of the present invention will become apparent from and elucidated with reference to the embodiments described hereinafter.

Exemplary embodiments of the present invention will be described in the following with reference to the following drawings.

Figure 1:
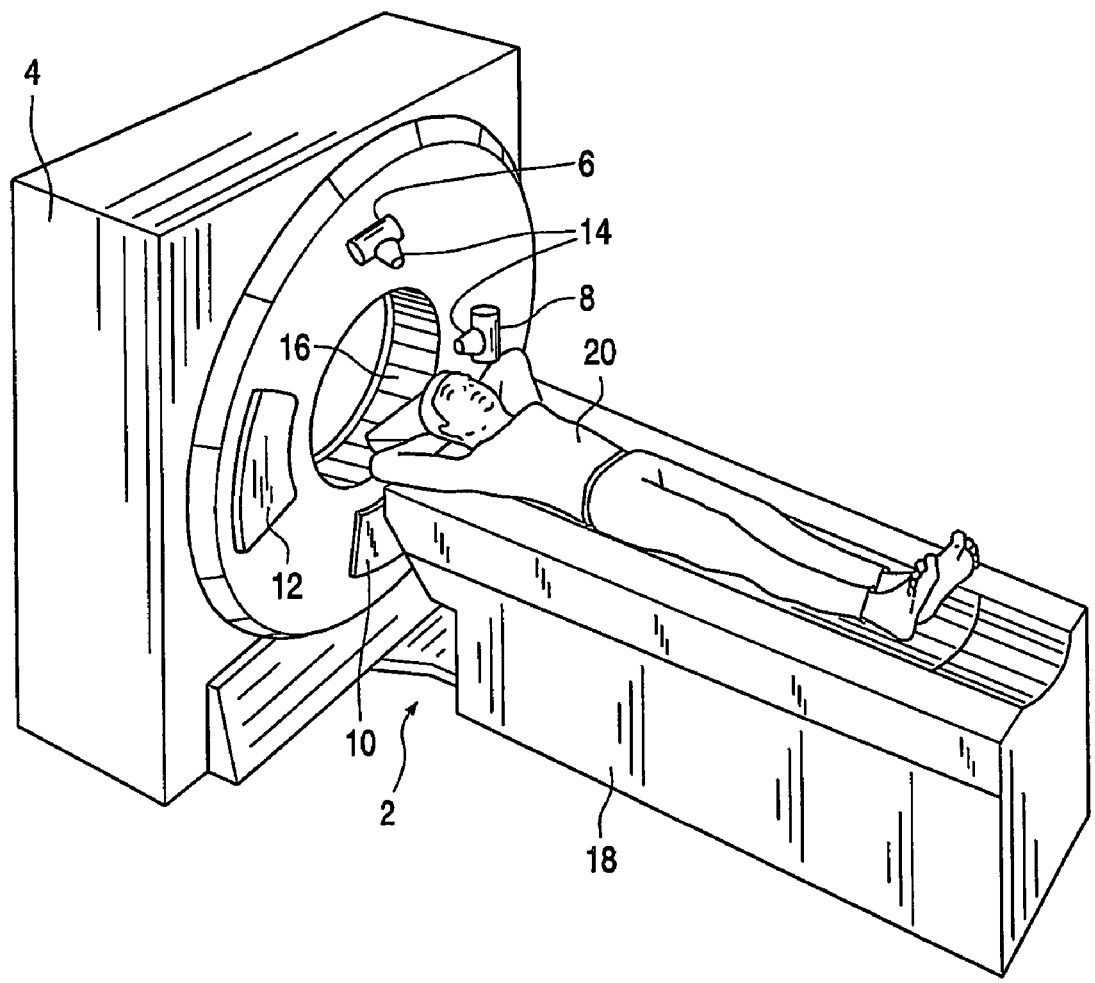
FIG. 1 shows a pictorial view of an exemplary embodiment of a CT imaging system according to the present invention.

FIG. 1 shows an exemplary embodiment of a computed tomograph (CT) imaging system 2 according to the present invention. The CT system 2 is shown as including a gantry 4. The gantry 4 is provided with two source-detector pairs, namely a first source-detector pair consisting of a first radiation source 6 and a first radiation detector 6 and a second source-radiation pair, consisting of a second radiation source 8 and a second radiation detector 12. The source-detector pairs are arranged on the gantry 4 such that the first and second radiation sources 6 and 8 are respectively arranged on opposite sides of the respective corresponding one of the first and second radiation detectors 10 and 12. A radiation emitted from the first and second radiation sources 6 and 8 respectively projects from a focal spot 14 provided at each of the first and second radiation sources 6 and 8 and extends—after being suitably collimated—through an examination area including the gantry opening 16 to the corresponding one of the first and second radiation detectors 10 and 12.

Reference character 18 designates a table for supporting a patient 20 to be examined. During examination, the patient 20 on the table 18 is translated along an axis through the center of the gantry opening 16 while the gantry rotates the source-detector assemblies around the patient 20 such that a helical scan path is achieved in a coordinate system attached to the patient.

Figure 2:
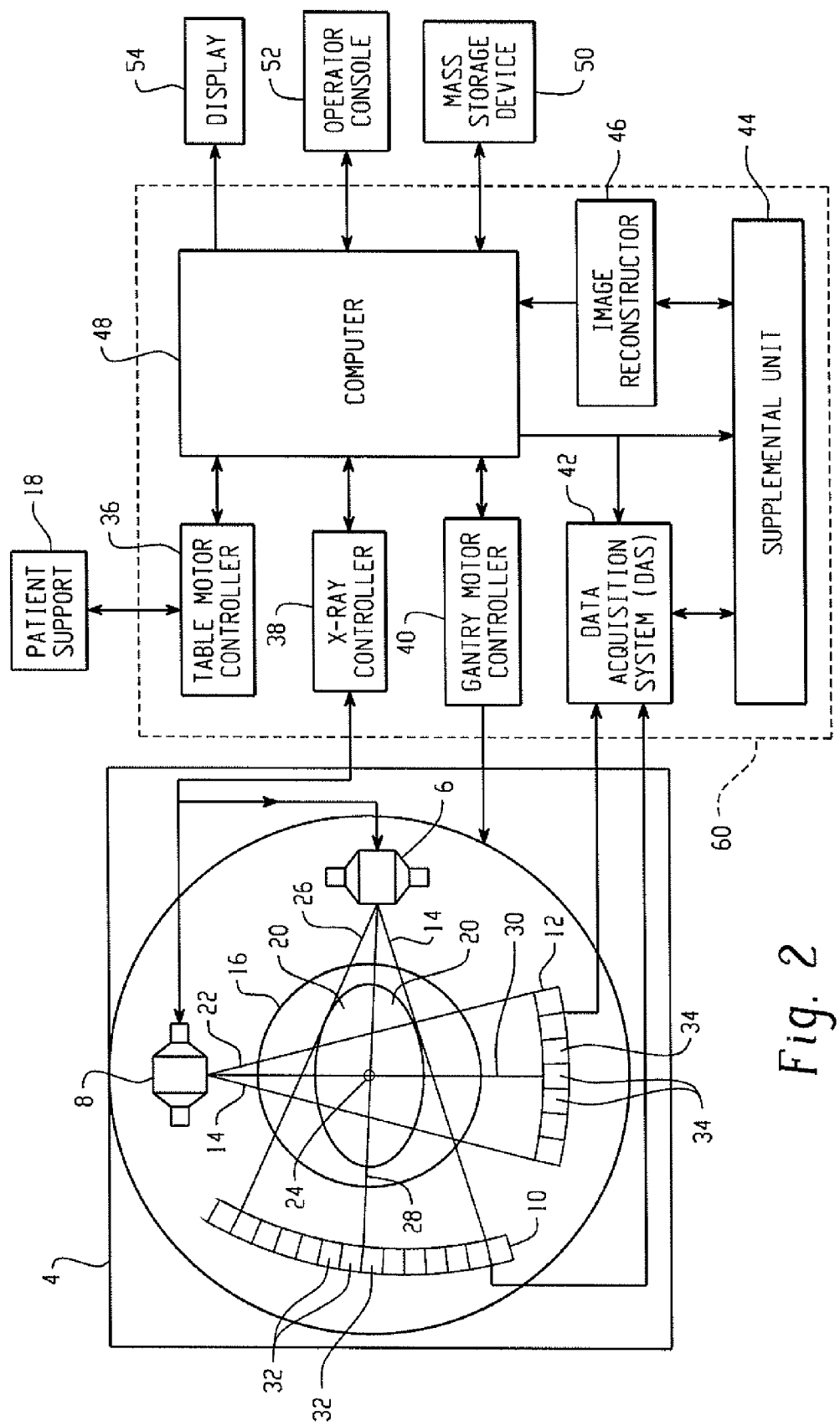
FIG. 2 shows a block schematic diagram of the system illustrated in FIG. 1

FIG. 2 shows a block schematic diagram of the system illustrated in FIG. 1. In FIG. 2, the same reference characters are used to designate the same or corresponding elements as in FIG. 1.

From the focal spot 14 of the first radiation source 6, a first radiation beam 26 is emitted such that it projects through the gantry opening 16 such that the patient 20 lying within the gantry opening 16 is within the x-ray beam 26. The first radiation detector 10 provided opposite to the first radiation source 16 with respect to the gantry opening 6 has dimensions corresponding to the form of the first radiation beam 26. The first radiation beam 26 extends along the first beam plane 28. Beam plane 28, generally referred to as the "fan-beam plane", contains the center line of focal spot 14 and the center line of the first x-ray beam 26 of the first radiation source 6. The first radiation detector 10 comprises a first number of detector elements or cells 32 for transforming the attenuated radiation into electrical signals.

The second radiation source 8 is provided on the gantry 4 such that it emits a second x-ray beam 22 from the focal spot 14 towards the second detector 12 arranged on the opposite side of the gantry 4 with respect to the gantry opening 16. The second x-ray beam 22 extends from the second radiation source 8 along the second beam plane 30.

Each of the first and second x-ray beams 22 and 26 are collimated by a collimator (not shown) to lie within a X-Y plane of a Cartesian coordinate system and generally referred to as an "imaging plane". As the first radiation detector 10, the second radiation detector 12 is formed by a plurality of second detector elements 34, which together sense the projected x-rays of the second x-ray beam 22 that pass through the medical patient 20 in the gantry opening 16. Preferably, the first and second radiation detectors 10 and 12 are respectively formed by an X-Y array of detector elements 32 and 34. Also, each of the first and second radiation detectors 10 and 12 may be a single slice detector or a multi-slice detector. Each of the first and second detector elements or cells 32 or 34 produce an electrical signal that represents the intensity of an impinging x-ray beam and represents the integral attenuation of the beam as it passes through the patient 20. During a scan to acquire x-ray protection data, the gantry 4 and all the components mounted thereon rotate about a center of rotation 24 while the patient 20 is translated along a normal to the plane in which the gantry 4 rotates.

As can be seen from FIGS. 1 and 2, the first and second source-detector assemblies are angularly displaced about the gantry, preferably at an angle of 90°.

The first and second radiation sources 6 and 8 are connected to an x-ray controller 38 for controlling operation of the first and second radiation sources 6 and 8. In particular, the x-ray controller 36 provides power and timing signals to the first and second radiation sources 6 and 8. Furthermore, there is provided a gantry motor controller 40 for controlling the rotational speed and position of the gantry 4.

Reference character 42 designates a data acquisition system (DAS) sampling analog data from the first and second detector elements 32 and 34 of the first and second radiation detectors 10 and 12 and converting the data to digital signals for subsequent processing.

Reference character 36 designates a table motor controller connected to a computer 48 for controlling the motorized table 18 to position patient 20 in the gantry 4 and to control the translation movement of the patient 20 through the gantry opening 16 during a scan.

The computer 48 is connected to the table motor controller 36, the x-ray controller 38, the gantry motor controller 40, the DAS 42, a supplementation unit 44 and an image reconstructor 46. Furthermore, the computer 44 is connected to a mass storage 50, to an operator console 52 by which an operator may control the operation of the CT system and to a display 54 via which the final image may be displayed to the operator.

The supplementation unit 44 receives sampled and digitized x-ray data from the DAS 42 and supplements second readouts from the second radiation detector 12 with elements from a first readout from the first radiation detector 10. In particular, since a first surface area of the first radiation detector 10 exceeds a second surface area of the second radiation detector 12 by a third surface area, the supplementation unit 44 generates a first complete data set from the first readout and a second complete data set from the first and second readouts, wherein the second complete data set comprises readouts corresponding to the third surface area. In other words, the supplementation unit 44 supplements the second readout from the detector cells 44 of the second radiation detector 12 with readouts from the first detector cells 32 from the first radiation detector 10. Preferably the first readouts used for supplementing second readouts from the second radiation detector 12 are derived from readings from first detector cells 32 in a surface area of the first radiation detector 10 exceeding the surface area of the second radiation detector 12. Hence, the supplementation unit 44 generates two complete data sets wherein the first complete data set comprises the readings of the first detector cells 32 of the first radiation detector 10 whereas the second complete data set comprises readings of the second detector cells 34 of the second radiation detector 12 and readings of the first detector cells 32 of the first radiation detector 10. By this, a simulation is made that the second radiation detector 12 has the same amount of detector cells or the same surface as the first radiation detector 10. The complete first and second data sets are transmitted to the image reconstructor 46, which performs a high-speed image reconstruction. Since the first and second complete data sets simulate data sets of a CT system, where two radiation detectors having the same size or the same amount of detector cells are provided, the high-speed image reconstruction can be performed in the same manner as known in the art. The reconstructed image is applied as an input to the computer 48, which stores the image in the mass storage device 50.

Operator supplied commands input to the computer 48 via the operator console 52 are used by the computer 48 to provide control signals and information to the table motor controller 36, the x-ray controller 38, the gantry motor controller 40, to the DAS 42 to the supplementation unit 44, to the image reconstructor 46, to the mass storage 50 and to the display 54.

Figure 3:
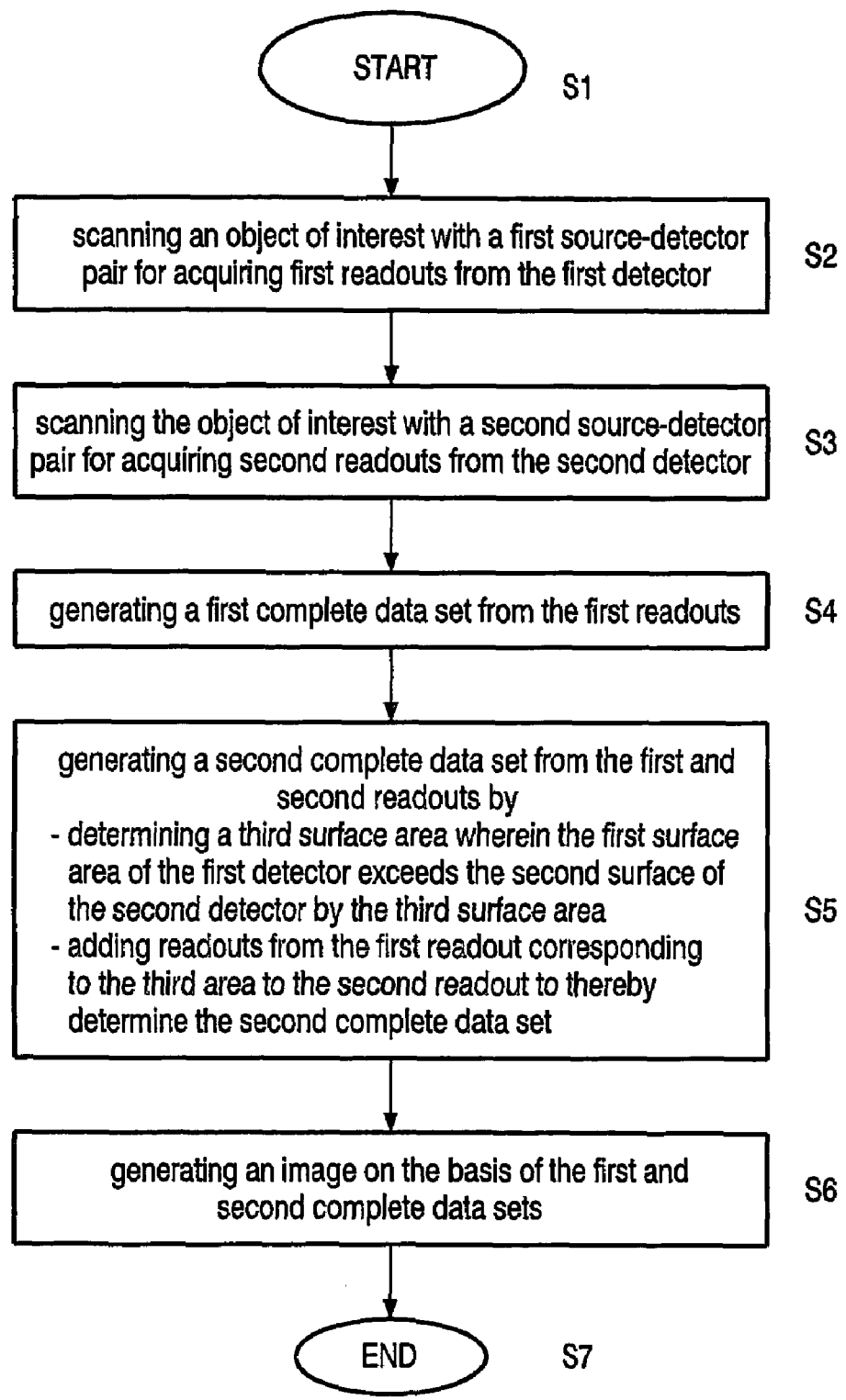
FIG. 3 is a flow-chart illustrating an exemplary embodiment of a sequence of steps executed by the CT imaging system of FIGS. 1 and 2.

In the following, an exemplary embodiment of an operation of the CT system of FIGS. 1 and 2 is described with reference to FIG. 3 showing a flow-chart of an exemplary embodiment of a method for operating a CT system according to the present invention.

After the start in step S1, the object of interest 20 is scanned with the first source-detector pair 6, 10 for acquiring first readouts from the first radiation detector 10. Simultaneously to the scan with the first source-detector pair 6, 10, the object of interest 20 is scanned in step S3 with the second source-detector pair 8, 12 for acquiring second readouts from the second radiation detector 12. During this, the computer controls the table motor controller 36 and therewith table 18 such that the table translates the patient 20 along the axis, which is normal to the rotational plane of the gantry 4. Also, computer 48 controls the x-ray controller 38 such that the first and second radiation sources 6 and 8 emit adequate amounts of radiation. Furthermore, during steps S2 and S3, the computer 48 controls the gantry motor controller 40 for rotation around the center of rotation 30 to cause the helical scan path.

In a subsequent step S4, the data provided from DAS 42 to the supplementation unit 44 is used for generating a first complete data set from the first readout. In other words, a first complete data set is generated consisting of information corresponding to sample values of the first detector elements 32. The first complete data set may be provided to the image reconstructor 46. Then, the method continues to step S5.

In step S5, the supplementation unit 44 generates a second complete data set from the first and second readouts. As already mentioned above, the first readouts are the readings of the first detector elements 32 during the scan. The second readouts are the readings or detection results of the detector elements 34 of the second radiation detector 12 during the scan.

In step S5, the supplementation unit 44 determines a first surface area of the first radiation detector 10 by which the surface of the first radiation detector exceeds the surface of the second radiation detector 12. This exceeding surface area is referred to as third surface area.

Then, the supplementation unit 44 adds readouts derived from the first readout corresponding to the third area, to the second readout, to thereby generate the second complete data set.

The operation in step S5 will be described in further detail with reference to FIGS. 4 and 5.

Figure 4:
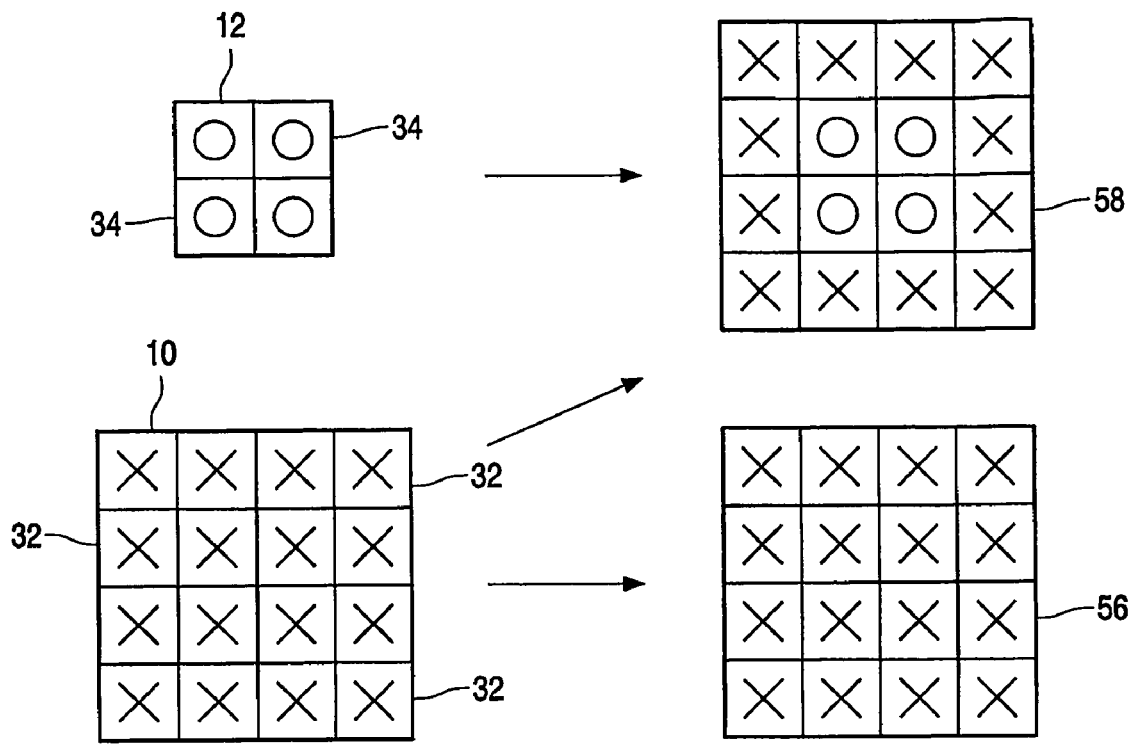
FIG. 4 is a simplified illustration for further explaining step S5 of FIG. 3.

FIG. 4 shows an illustration for further explaining the supplementation of the second readouts to form the second complete data set. As in FIGS. 1 and 2, reference character 12 designates the second detector element. The second detector element 12 shown in FIG. 4 has four detector elements or cells 34. The sampling results of the four detector elements 34 of the second radiation detector 12 are symbolized with a circle.

Reference character 10 designates the first radiation detector consisting of sixteen first detector cells or elements 32. The sampling results of the first detector cells 32 are symbolized with a cross.

For forming a first complete data set 56, information corresponding to the sampling results of the first detector cells 32 is used as symbolized with the crosses in the first complete data set 56.

As can be seen from the second complete data set 58, the sampling results from the second detector cells 34 of the second radiation detector 12 are used to derive the respective data for the corresponding area of the second complete data set 58. However, as may be taken from FIG. 4, sampling results from the first detector cells 32 are used to complete the second complete data set 58. When these two data sets, 56 and 58, are transmitted to the image reconstructor 46, a CT system is simulated, having two detectors of the same size. According to an exemplary embodiment, the missing data should not be substituted 1:1, since, due to the movement of the table 18, the data from the first detector cells 32 corresponds to a different z-position. Thus, a suitable correction method may be applied to derive the missing data with a corresponding z-position from the readouts from the first detector cells 32 to supplement the readouts form the second detector cells 34.

However, since according to the present invention the second radiation detector 12 has a significant smaller surface and a significant smaller amount of second detector elements 34, a radiation power emitted from the second radiation source 8 can be reduced significantly, such that a radiation dose to which the patient 20 is subjected can be reduced significantly. Moreover, according to the present invention, the costs for the source-detector assembly can be kept low and less space is occupied on the gantry.

Figure 5:
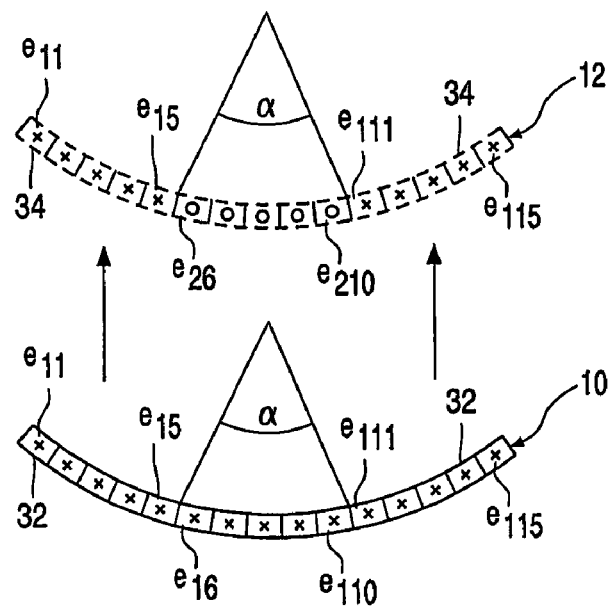
FIG. 5 is another simplified illustration for further explaining step S5 of FIG. 3.

FIG. 5 illustrates another exemplary embodiment of the present invention. Here, line detectors are used as first and second radiation detectors 10 and 12. In FIG. 5, the same reference characters are used as in FIGS. 1 to 4 to denote the same or similar components. The first readout from the first radiation detector 10 consists of sampling results from the detector cells $e_{11}$ to $e_{115}$ of the first detector cells 32. The second readout consists of sampling results of the detector cells $e_{26}$ to $e_{210}$ of the second detector cells 34. For generating the second complete data sets, the sampling results from detector cells $e_{11}$ to $e_{15}$ and $e_{111}$ to $e_{115}$ from the first detector cells 32 are used to derive data to supplement the sampling results from the detector cells $e_{26}$ to $e_{210}$ of the second detector cells 34.

Then, after step S5, the method continues to step S6 where the image reconstructor 46 generates an image on the basis of the first and second complete data sets. Then, from step S6, the method continues to step S7 where it ends.

As indicated by box 60, drawn with broken lines, instead of providing an individual device for the table motor controller 36, the x-ray controller 38, the gantry motor 40, the DAS 42, the supplementation unit 44, the image reconstructor 46 and the computer, a single calculation unit may be provided for performing the operation of the individual components.

Figure 6:
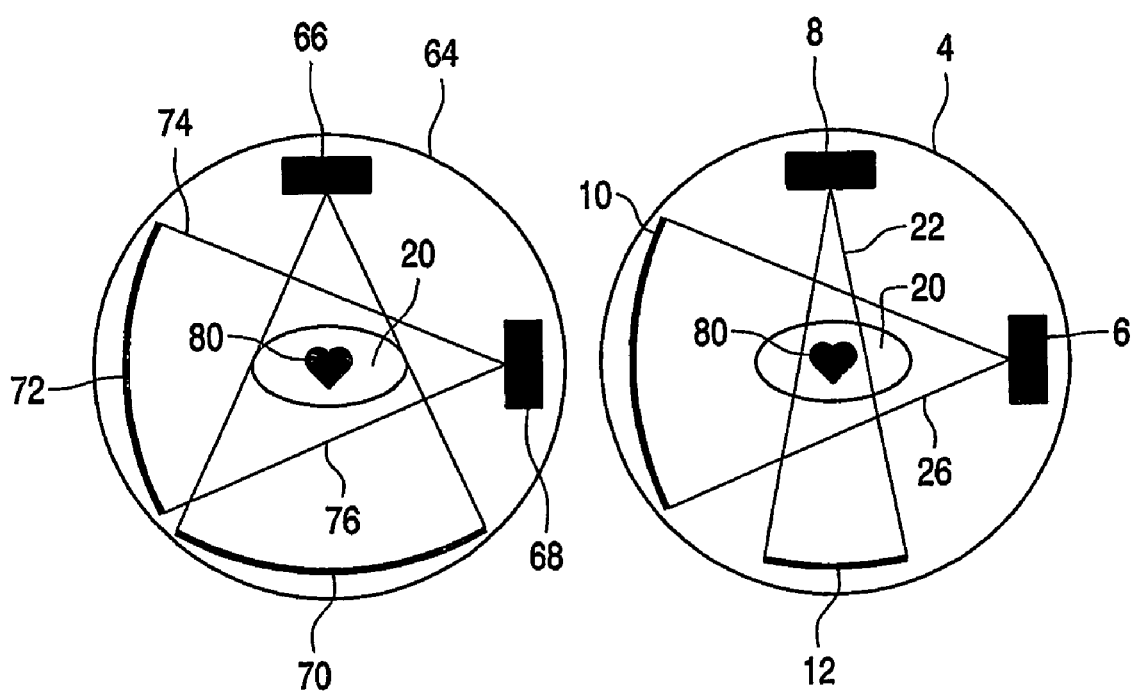
FIG. 6 is a simplified illustration of an exemplary embodiment of a CT imaging system according to the present invention for further explaining aspects of the present invention.

FIG. 6 is a simplified illustration for explaining an aspect of an exemplary embodiment of the present invention. On the left side of FIG. 6, a CT system with a gantry 64 as known in the art is shown. Such a known system comprises first and second radiation sources 66 and 68 and first and second radiation detectors 70 and 72. As can be seen from the left side of FIG. 4, the radiation detectors 70 and 72 have the same size.

According to the present invention as shown on the right side of FIG. 6, a gantry 4 is provided, comprising first and second radiation sources 6 and 8 and first and second radiation detectors 10 and 12. As can be taken from the right side of FIG. 6, the second radiation detector 12 is significantly smaller than the first radiation detector 10. Accordingly, the radiation detector 12 is cheaper and allows to thereby reduce overall costs for the CT system. Moreover, as can be seen by the angle of the radiation beam 22, in comparison to the angle of the radiation beams 26, 74 and 76, a radiation dose subjected to the patient 20 is reduced significantly in comparison to the CT system with the gantry 64 shown on the left side of FIG. 6. According to the present invention, the dose reduction may be achieved by collimation of the radiation beam 22. Furthermore, for dose reduction, a Focal Spot may be implemented.

According to another aspect of the present invention, in order to generate images of a certain phase of the heart of the patient 20, the CT system shown in FIGS. 1 and 2 may be linked to a ECG signal, which may be utilized to collect projection data during known periods of reduced motion of the heart or of a certain phase of the heart. Preferably, the present invention may be applied to a dose minimized dual tube cardiac CT.

As shown in FIG. 6, the second source-detector assembly is adopted such that it illuminates only the heart region 80 of the patient. As indicated above, the respective projections (of the vertical beam arrangement) will be incomplete. However, since the patient holds his breath, motion occurs only in the heart and not in other parts of the body. Due to this, the missing data can be substituted once it has been obtained form the following or preceding first source detector arrangement 6, 10. Once the missing data in the projections has been substituted as described above, the complete data set can be reconstructed and the high temporal resolution is retained in the same manner as with the two identical source-detector assemblies as shown on the left side of FIG. 6.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A computerized tomographic imaging system for generating an image of an object of interest, the system comprising:
    a first source-detector pair mounted to rotate around the object of interest, wherein the first source-detector pair comprises a first radiation source and a first radiation detector having a first number of detector elements, wherein the first radiation source emits a first radiation beam towards the first radiation detector with a first radiation power per detector element such that the first radiation beam traverses the object of interest and impinges onto the first radiation detector;

a second source-detector pair mounted to rotate around the object of interest, wherein the second source-detector pair comprises a second radiation source and a second radiation detector with a second number of detector elements, wherein the second radiation source emits a second radiation beam towards the second radiation detector with a second radiation power per detector element such that the second radiation beam traverses the object of interest and impinges onto the second radiation detector;

wherein the second number of detector elements is smaller than the first number of detector elements and the first radiation power per detector element matches the second radiation power per detector element and a first surface area of the first radiation detector exceeds a second surface area of the second radiation detector by a third surface area;

a supplementation unit which generates a first complete data set from a first radiation detector readouts and a second data set from a second radiation detector readouts in combination with a portion of the first data set corresponding to the third surface area, such that two complete data sets are generated;

a reconstruction processor for reconstructing an image representation from the first and second complete data sets.

2. The computerized tomographic imaging system of claim 1, further comprising:
a gantry; wherein the first and second source-detector pairs are angularly displaced about the gantry.

3. The computerized tomographic imaging system of claim 1, wherein the computerized tomographic imaging system is a dual tube cardiac CT system.

4. The computerized tomographic imaging system of claim 1, wherein the object of interest is a heart, wherein the first radiation beam spans a patient's torso and the first detector receives radiation from the first radiation source that spans the patient's torso and the second radiation spans the patient's heart and the second radiation detector receives radiation from the second radiation source that spans the patient's heart, wherein the supplementation unit combines a portion of the first radiation detector read outs which corresponds to the third cross-sectional area with second radiation detector readouts are collected at a common angular orientation of the first and second radiation beams and at a different cardiac phase.

5. The computerized tomographic imaging system of claim 1, further including:
a cardiac monitor;
sorting data of the first complete data set and the second complete data set by cardiac phase;
wherein the reconstruction processor reconstructs portions of the first and second complete data sets which correspond to the same cardiac phase into an image representation of the cardiac phase.

6. A computer program comprising computer program code to execute the following steps when the computer program code is executed on a computerized tomographic imaging system:
scanning the object of interest by means of a first source-detector pair, wherein the first source-detector air comprises a first radiation source and a first radiation detector, wherein the first radiation source emits a first radiation beam towards the first radiation detector such that the first radiation beam traverses the object of interest and impinges onto the first radiation detector; and
scanning the object of interest by means of a second source-detector pair, wherein the second source-detector pair comprises a second radiation source and a second radiation detector, wherein the second radiation source emits a second radiation beam towards the second radiation detector such that the second radiation beam traverses the object of interest and impinges onto the second radiation detector;
reading first readouts from the first radiation detector and second readouts from the second radiation detector; and
generating the image from the first and second readouts;
wherein, for generating the image, a first number of elements from the first readout and a second number of elements from the second readout are used; wherein the first number of elements corresponds to first detector elements of the first radiation detector; wherein the second number of elements corresponds to second detector elements of the second radiation detector; and wherein the second number is smaller than the first number,
wherein a first surface area of the first radiation detector exceeds a second surface area of the second radiation detector by a third surface area, wherein the program code further executes the steps of:
generating a first complete data set from the first readout and a second complete readout from the first and second readouts;
wherein the second complete data set comprises readouts corresponding to the third surface area.

7. A method of generating an image of an object of interest, the method comprising:
scanning an object of interest with a first source-detector pair including a first radiation source that generates a first cone beam of radiation and a first radiation detector which receives the first cone beam of radiation, the first radiation detector having a first array of detector elements, which first array has a first cross-sectional area;
scanning an object of interest with a second source-detector pair including a second radiation source that generates a second cone beam of radiation and a second radiation detector which receives the second cone beam of radiation, the second radiation detector having a second array of detector elements, which second array has a first cross-sectional area, the second array cross-sectional area being larger than the second array cross-sectional area, a difference between the first array cross-sectional area and the second array cross-sectional area being a third cross-sectional area;
rotating the first and second source-detector pairs concurrently around the object of interest to generate a first set of data and a second set of data;
copying a portion of the first data set corresponding to the third cross-sectional area and combining the copied portion with the second data set at corresponding angular orientations of the first and second source-detector pairs to form a supplemental second data set such that the first data set and the supplemental second data set both represent data collected over the first cross-sectional area;
reconstructing the first data set and the supplemented second data set into a common image representation.

8. The method of claim 7, wherein the method is for operating a dual tube cardiac CT system.

9. The method of claim 7, wherein the object of interest is a heart, wherein the first cone beam spans a patient's torso and the first detector receives radiation from the first radiation source that spans the patient's torso and the second cone beam spans the patient's heart and the second detector receives radiation from the second radiation source that spans the patient's heart, wherein in the combining step, data from the first data set which corresponds to the third cross-sectional area is combined with data of the second data set which is collected at a common angular orientation of the radiation cone beam and at a different cardiac phase.

10. The method of claim 9, further including:
sorting data of the first data set and the supplemented second data set by cardiac phase;
reconstructing portions of the first and supplemented second data sets which correspond to the same cardiac phase into an image representation of the cardiac phase.

11. A computerized tomographic imaging system including a system controller programmed to control the tomographic imaging system to perform the method of claim 7.

12. A computer program product carrying computer code for controlling a computer to perform the steps of claim 7.

* * * * *